United States Patent [19]
Gobbini et al.

[11] Patent Number: 5,489,582
[45] Date of Patent: * Feb. 6, 1996

[54] 14-DEOXY-14α-CARDENOLIDES 3β-THIODERIVATIVES AND PHARMACEUTICAL COMPOSITION COMPRISING SAME FOR TREATING CARDIOVASCULAR DISORDERS

[75] Inventors: Mauro Gobbini, Mercallo; Luigi Bernardi; Mara Ferrandi, both of Milan; Piero Melloni, Bresso; Luisa Quadri, Cernusco; Roberto Villa, Milan, all of Italy

[73] Assignee: Sigma-Tau Industrie Farmaceutiche Riuntie S.p.A, Rome, Italy

[*] Notice: The portion of the term of this patent subsequent to Dec. 26, 2012, has been disclaimed.

[21] Appl. No.: 80,525

[22] Filed: Jun. 24, 1993

[30] Foreign Application Priority Data

Jul. 1, 1992 [DE] Germany .......................... 42 21 538.2

[51] Int. Cl.$^6$ ...................... C07D 405/12; A61K 31/585
[52] U.S. Cl. .......................... 514/175; 540/102; 540/107; 540/108
[58] Field of Search ................... 540/102, 107, 540/108; 514/175

[56] References Cited

U.S. PATENT DOCUMENTS 4,259,240 3/1981 Miesner et al. ................ 260/239.99 R

FOREIGN PATENT DOCUMENTS 1038294 9/1978 Canada .
2833472 6/1980 Germany .

OTHER PUBLICATIONS

Stache, Tetrahedron Letters No. 42 pp. 3897–3880 (1971),

Donovan et al., Tetrahedron Letters No. 35, pp. 3287–3290 (1979).

Bobbio, J. Org. Chem 1961 vol. 26 (pp. 3023–3024).

Fritsch et al, Liebigs Ann. Chem 1966 pp. 195–205.

Kreiser et al, Liebigs Ann. Chem. 1972 pp. 12–16.

Erdman, Arzneim Forsch 1984 vol. 34 1314.

Naidoo et al, J. Pharm. Sciences 1974 vol. 63, pp. 1391–1394.

Jorgensen, Biochimica et Biophysica Acta 1974 356 pp. 36–52.

*Primary Examiner*—Nicholas Rizzo
*Attorney, Agent, or Firm*—Oblon, Spivak, McClelland, Maier & Neustadt

[57] ABSTRACT

14-Deoxy-14α-cardenolides 3β-thioderivatives and pharmaceutical compositions comprising same for treating cardiovascular disorders, such as heart failure and hypertension, are disclosed.

19 Claims, No Drawings

14-DEOXY-14α-CARDENOLIDES 3β-THIODERIVATIVES AND PHARMACEUTICAL COMPOSITION COMPRISING SAME FOR TREATING CARDIOVASCULAR DISORDERS

The present invention relates to 14-deoxy-14α-cardenolide 3β-thioderivatives, a process for their preparation and pharmaceutical compositions containing same for the treatment of cardiovascular disorders such as heart failure and hypertension.

The compounds of the present invention have formula (I):

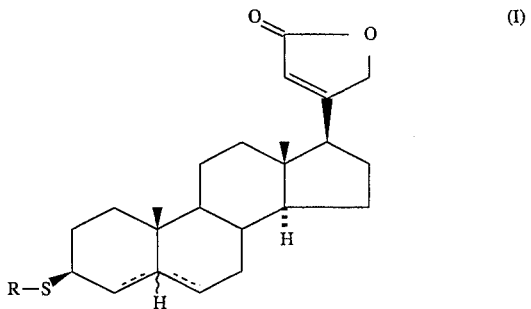

wherein:
the symbol $\equiv$ represents a single or a double bond;
R is C2–C6 alkyl or C3–C6 alkenyl, unsubstituted or substituted independently by a quaternary ammonium group, a 2-(2-imidazolinyl) group or one or more OR1 or NR2R3 or C(NH)NR4R5;

wherein:
R1 is H, methyl or C2–C4 alkyl substituted by NR6R7 with the proviso that when R1 is H, R is C3–C6 substituted alkyl and at least another group chosen from NR2R3 or C(NH)NR2R3 is also present in the R residue;

R2, R3 are independently H, methyl or C2–C6 alkyl unsubstituted or substituted by NR6R7 or C3–C6 alkenyl or R2 and R3 taken together with the nitrogen atom form an unsubstituted or substituted saturated or unsaturated heteromonocyclic ring optionally containing another heteroatom chosen from oxygen or sulfur or nitrogen, or R2 is hydrogen and R3 is C(NH)NH2;

R4, R5 are independently H, C1–C4 alkyl or C3–C4 alkenyl or R4 and R5 taken together with the nitrogen atom form a penta- or hexa-monoheterocyclic ring;

R6, R7 are independently H, C1–C4 alkyl or R6 and R7 taken together form with the nitrogen atom a saturated or unsaturated penta- or hexa-monoheterocyclic ring optionally containing another heteroatom chosen from oxygen or sulfur or nitrogen or R6 is hydrogen and R7 is C(NH)NH2.

The invention includes within its scope all the possible stereoisomers, in particular E and Z isomers, optical isomers and their mixtures and the metabolites and the metabolic precursors of the compounds of formula (I). In particular if $\equiv$ is a single bond both the 5α and 5β isomers are encompassed within the scope of the present invention.

Pharmaceutical acceptable salts of (I) are salts which retain the biologically activity of the base and are derived from such known pharmacologically accetable acids such as e.g. hydrochloric, sulfuric, phosphoric, malic, tartaric, maleic, citric, methanesulfonic or benzoic acid.

The alkyl and alkenyl groups may be branched or straight chain groups.

The C2–C6 alkyl group is preferably a C2–C4 alkyl group, e.g. ethyl, propyl, isopropyl, butyl, sec-butyl.

The C3–C6 alkenyl group is preferably a C3–C4 alkenyl group.

The quaternary ammonium group is preferably a trimethylammonium- or a N-methylpyrrolidinium- or a N-methylpiperidinium- group.

The OR1 group is preferably hydroxy, 2-aminoethoxy, 3-aminopropoxy, 2-dimethylaminoethoxy, 3-dimethylaminopropoxy, 3-amino-2-hydroxypropoxy, 2,3-diaminopropoxy, 2-(1-pyrrolidinyl)ethoxy, 3-(1-pyrrolidinyl)propoxy.

The NR2R3 group is preferably amino, methylamino, ethylamino, propylamino, isopropylamino, allylamino, propargylamino, dimethylamino, pyrrolidinyl, morpholino, piperazinyl, imidazolyl, guanidino, 2-aminoethylamino, 3-aminopropylamino, 2-(1-pyrrolidinyl)ethylamino, 3-(1-pyrrolidinyl)propylamino.

The C(NH)NR4R5 group is preferably a primary amidino group.

The NR6R7 is preferably amino, methylamino, ethylamino, propylamino, dimethylamino, pyrrolidinyl, morpholino, piperazinyl or imidazolyl.

Preferred examples of specific compounds according to the present invention are:

3β-(2-(N-Methyl-N-pyrrolidinium)ethylthio)-5β,14α-card-20(22)-enolide chloride
3β-(2-Aminoethylthio)-5β,14α-card-20(22)-enolide
3β-(3-Aminopropylthio)-5β,14α-card-20(22)-enolide
3β-(2-Aminoethylthio)-14α-card-4,20(22)-dienolide
3β-(3-Aminopropylthio)-14α-card-4,20(22)-dienolide
3β-(2-(1-Pyrrolidinyl)ethylthio)-14α-card-4,20(22)-dienolide
3β-(3-(1-Pyrrolidinyl)propylthio)-14α-card-4,20(22)-dienolide
3β-(2-Aminoethylthio)-14α-card-5,20(22)-dienolide
3β-(3-Aminopropylthio)-14α-card-5,20(22)-dienolide
3β-(2-(1-Pyrrolidinyl)ethylthio)-14α-card-5,20(22)-dienolide
3β-(3-(1-Pyrrolidinyl)propylthio)-14α-card-5,20(22)-dienolide
3β-(2-Aminoethylthio)-5α,14α-card-20(22)-enolide
3β-(3-Aminopropylthio)-5α,14α-card-20(22)-enolide
3β-(2-(1-Pyrrolidinyl)ethylthio)-5α,14α-card-20(22)-enolide
3β-(3-(1-Pyrrolidinyl)propylthio)-5α,14α-card-20(22)-enolide
3β-(4-Amino-(E)-2-butenylthio)-5β,14α-card-20(22)-enolide
3β-(2-Methylaminopropylthio)-5β,14α-card-20(22)-enolide
3β-(2-Dimethylaminopropylthio)-5β,14α-card-20(22)-enolide
3β-(2-(1-Pyrrolidinyl)ethylthio)-5β,14α-card-20(22)-enolide
3β-(3-(1-Pyrrolidinyl)propylthio)-5β,14α-card-20(22)-enolide
3β-(2-Morpholinoethylthio)-5β,14α-card-20(22)-enolide
3β-(2-(1-Piperazinyl)ethylthio)-5β,14α-card-20(22)-enolide
3β-(3-(1-Piperazinyl)propylthio)-5β,14α-card-20(22)-enolide
3β-(2-(1-Imidazolyl)ethylthio)-5β,14α-card-20(22)-enolide
3β-(2-(2-Amidino)ethylthio)-5β,14α-card-20(22)-enolide
3β-(2-Guanidinoethylthio)-5β,14α-card-20(22)-enolide
3β-(3-Amino-2-hydroxypropylthio)-5β,14α-card-20(22)-enolide
3-(2,3-Diaminopropylthio)-5β,14α-card-20(22)-enolide 3β-(3-(1-Pyrrolidinyl)-2-hydroxypropylthio)-5β,14α-card-20(22)-enolide 3β-(3-(1-Piperazinyl)-2-hydroxypropylthio)-5β,14α-card-20(22)-enolide 3β-(3-(1-Imidazolyl)-2-hydroxypropylthio)-5β,14α-card-20(22)-enolide 3β-(3-Guanidino-2-hydroxypropylthio)-5β,14α-card-20(22)-enolide 3β-(3-(3-Amino-2-hydroxypropoxy)propylthio)-5β,14α-card-20(22)-enolide 3β-(3-(3-Amino-2-hydroxypropylamino)propylthio)-5β,14α-card- 20(22)-enolide The invention furthermore provides a process for the preparation of said compounds (I), which comprises condensing the compounds having formula (II) where ⁓ is as above defined

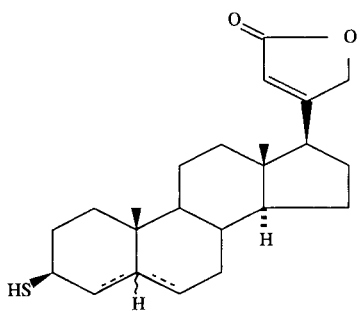

with a compound of formula (III)

R—Y    (III)

where Y is an electron-withdrawing group, such as halogen, mesyloxy, or tosyloxy group, which confers electrophilic properties to the attached carbon atom, and R is as above defined, the hydroxy and amino groups, if any, present in R being protected, if necessary, with methods well known to those skilled in the art to give, after removal of the protective groups, if any, compounds of general formula (I) which may be converted into other compounds of formula (I) and optionally converting compounds (I) into pharmaceutically acceptable salts thereof and optionally separating a mixture of isomers into single isomers.

The condensation reaction between (II) and (III) is best carried out in an inert aprotic solvent, such as tetrahydrofuran, dioxane, dimethylformamide, dimethylsulfoxyde or in the neat (III) and in the presence of a strong base e.g. sodium or potassium hydride at a temperature ranging from −20° C. to about 60° C.

Due to the presence of a lactone function, care has to be taken to avoid a basic pH during the work-up.

The purifications are best performed by flash-chromatography on silica gel.

In the literature the thiols are normally obtained by reduction of acylthio derivatives with lithium aluminum hydride (Bobbio P. A., *J. Org. Chem.*, 1961, 26, 3023), method that cannot be used in this case due to the presence of a reducible lacton function. It has been found that the free thiols can be obtained by ammonolysis of the acetylthio derivative (IV).

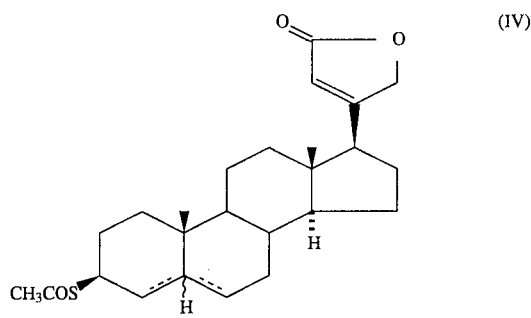

The acetylthio derivatives (IV) are new and are obtained by reaction of the 3α-alcohols (V) with thiolacetic acid in the presence of a dialkyl azodicarboxylate and triphenylphosphine.

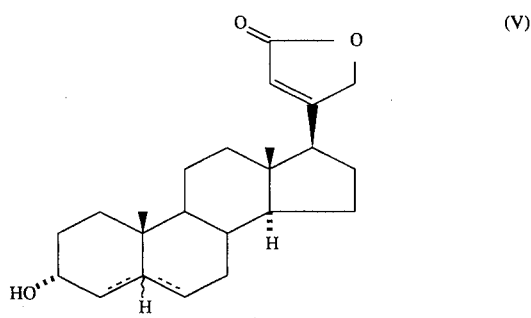

The 3α-hydroxy-5β,14α-card-20(22)-enolide (formula (V) wherein ⁓ are single bonds and the hydrogen in position 5 is β) is a known compound (Stake U., *Tetr. Lett.*, 1971, 3877) and is obtained by selective reduction of the corresponding 3-keto derivative (Donovan S. F., *Tetr. Lett.*, 1979, 3287) with a complex hydride.

The 3α-hydroxy-14α-card-4,20(22)-dienolide (formula (V) wherein ⁓ is a double bond in position 4; see Prep. 9) is new and is obtained by selective reduction of the corresponding 3-keto derivative with a complex hydride.

The 3α-hydroxy-14α-card-5,20(22)-dienolide (formula (V) wherein ⁓ is a double bond in position 5; see Prep. 10) is new and is obtained by selective reduction of the corresponding 3-keto derivative (VIa)(see Prep. 12) with a complex hydride.

The 3α-hydroxy-5α,14α-card-20(22)-enolide (formula (V) wherein ⁓ are single bonds and the hydrogen in position 5 is α; see Prep. 11) is new and is obtained by selective reduction of the corresponding 3-keto derivative (VIb) (see Prep. 13) with a complex hydride.

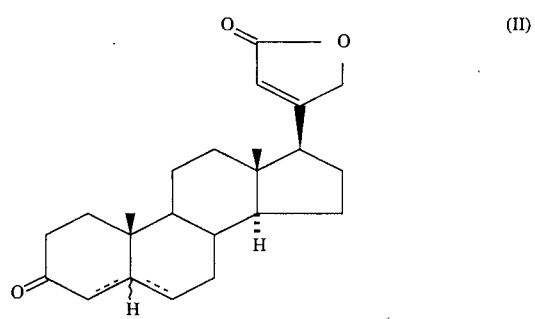

The intermediate 3-oxo-14α-card-4,20(22)-dienolide (formula (VI) wherein ⁓ is a double bond in position 4) is a known compound (Fritsch W. et al., *Liebigs Ann. Chem.* 1966, 699, 195). The 3-oxo-14α-card-5,20(22)-dienolide (formula (VI) wherein ⁓ is a double bond in position 5; see Prep. 12) is a new compound and is obtained by oxidation of the corresponding known 3β-hydroxy derivative (Fritsch W. et al., *Liebigs Ann. Chem.* 1966, 699, 195) with morpholine-N-oxide in the presence of a perruthenate salt.

The 3-oxo-5α,14α-card-20(22)-enolide (formula (VI) wherein ⁼ are single bonds and the hydrogen in position 5 is α; see Prep. 13) is a new compound and is obtained by oxidation of the corresponding known 3β-hydroxy derivative (Kreiser W. and Nazir M., *Liebigs Ann. Chem.* 1972, 755, 1) with morpholine-N-oxide in the presence of a perruthenate salt.

The compounds of general formula (III) are known compounds, generally commercially available or preparable from known compounds by known methods The 14-deoxy- 14α-derivatives of digitoxigenin was expected from the literature data (Naidoo B. K., et al., *J. Pharm. Sciences,* 1974, 63, 1391) to be practically devoid of inotropic effect; however, unexpectedly, the thioderivatives (I), prepared according to the invention and their pharmaceutically acceptable salts are useful agents for the treatment of cardiovascular disorders such as heart failure and hypertension and have low toxicity. Moreover said compounds (I) show high affinity for the receptor site of the $Na^+,K^+$-ATPase and behave as partial agonists on the enzymatic activity of the $Na^+,K^+$-ATPase.

To test the affinity for the receptor site of the $Na^+,K^+$-ATPase and the agonist or inhibitory activity on the enzyme, the following tests were used: a) displacement of the specific 3H-ouabain binding from the $Na^+,K^+$-ATPase receptor purified according to Jorghensen (Jorghensen P., *BBA,* 1974, 356, 36) and Erdmann (Erdmann E. et al., *Arzneim. Forsh.,* 1984, 34 (II), 1314); b) inhibition of the activity of the purified $Na^+,K^+$-ATPase measured as % of hydrolysis of $^{32}P$-ATP in presence and in absence of the tested compound (Mall F. et al., *Biochem. Pharmacol.,* 1984, 33, 47).

The ability of these compounds to lower blood pressure in adult hypertensive MHS rats was tested by the following method:

systolic blood pressure (SBP) and heart rate (HR) were measured by an indirect tail-cuff method in three-month old hypertensive MHS rats before beginning treatment (basal values). The rats were then subdivided in two groups of 7 animals each, one receiving the compound and the other, the control group, receiving only the vehicle. The compound, suspended in METHOCEL® 0.5% (w/v), for ten days, was administered daily by mouth. SBP and HR were measured daily 6 and 24 hours after the treatment. When ten-day treatment washout had been under way for at least two days, whether the treatment maintains SBP low or re-establish the basal values was verified.

The affinity and the inhibitory activity of some basic thioethers on the two tests are shown in the following table:

| Compound | Binding ³H-Ouab. Displacement -log. IC₅₀ | Inhibitory Activity -log. IC₅₀ |
| --- | --- | --- |
| DIGI | 6.5 | 6.5 |
| Comp. I-a | 5.5 | 5.3 |
| Comp. I-b | 6.0 | 5.5 |
| Comp. I-c | 6.1 | 5.8 |
| Comp. I-d | 5.9 | 5.7 |
| Comp. I-e | 5.7 | 5.4 |
| Comp. I-f | 5.9 | 5.5 |
| Comp. I-g | 6.0 | 5.7 |
| Comp. I-h | 5.8 | 5.4 |

The activity of the aglycone digitoxigenin (DIGI) and some basic thioethers in preventing the development of hypertension is shown in the following table:

| SYSTOLIC BLOOD PRESSURE FALL IN SPONTANEOUS HYPERTENSIVE RATS (MHS) | | | |
| --- | --- | --- | --- |
| Compound | RATS | DOSE* mg/Kg os | SBP mm Hg | HR beats/min. |
| Controls | 7 | METHOCEL® | 174 +/- 5.5 | 378 +/- 11.0 |
| DIGI | 7 | 20 | 173 +/- 4.0 | 380 +/- 10.0 |
| I-c | 7 | 20 | 144 +/- 6.2 | 390 +/- 12.0 |
| I-d | 7 | 20 | 154 +/- 5.2 | 384 +/- 10.3 |
| I-f | 7 | 20 | 148 +/- 5.6 | 386 +/- 9.3 |
| I-g | 7 | 20 | 150 +/- 5.2 | 383 +/- 9.6 |
| I-h | 7 | 20 | 158 +/- 5.4 | 379 +/- 10.4 |

*in METHOCEL® 0.5% w/v

The following examples illustrate the invention without limiting it.

EXAMPLE 1

3β-(2-(1-Pyrrolidinyl)ethylthio)-5β,14α-card-20(22)-enolide Oxalate (I-a)

a) To a solution of 0.13 g of 3β-mercapto-5β,14α-card-20(22)-enolide (II-a, Prep. 1) and 0.13 g of 1-(2-chloroethyl)pyrrolidine in 3.5 ml of dimethylformamide under nitrogen atmosphere at room temperature, 0.017 g of sodium hydride (60% dispersion in mineral oil) were added. The reaction mixture was stirred for 2.5 hrs, then 1.74 ml of 0.5N hydrochloric acid were added and the temperature was raised to 25° C. The mixture was extracted with methylene chloride, the organic layer was washed with water, dried over sodium sulfate, filtered and evaporated to dryness under reduced pressure. The crude product was purified by flash-chromatography ($SiO_2$) using methylene chloride/methanol/30% ammonia solution 95/5/1 as eluant; the pure compound (0.143 g) so obtained was dissolved in 2 ml of diethyl ether and a solution of 0.027 g of oxalic acid in 1.5 ml of diethyl ether was added to give 0.15 g of the title compound (I-a) as a white solid, mp 164°–166° C.

$^1H$-NMR (300 MHz, $CDCl_3$, ppm from TMS): 0.62 (3H, s); 0.98 (3H, s); 2.38 (1H, bt); 2.75–2.95 (4H, m); 3.20–3.42 (3H, m); 4.69 (1H, dd); 4.82 (1H, dd); 5.86 (1H, bs).

b) To 3β-mercapto-5β,14α-card-20(22)-enolide (II-a, Prep. 1) (0.35 g) in 5 ml of dimethylformamide under nitrogen atmosphere, 2-bromoethanol (0.2 ml) and 0.050 g of sodium hydride (60% dispersion in mineral oil) were added at 0° C. and the temperature left to raise to 25° C. After 5 hrs the reaction mixture was quenched with 0.5M HCl (0.22 ml) to neutralize the excess base and extracted with methylene chloride. The organic layer was washed with a 5% sodium bicarbonate solution, dried over anhydrous sodium sulfate and evaporated to dryness under reduced pressure. The crude product was purified by flash-cromatography ($SiO_2$) using n-hexane/ethyl acetate 50/50 as eluant to obtain 0.28 g of 3β-(2-hydroxyethylthio)-5β,14α-card-20(22)-enolide as a white solid.

$^1H$-NMR (300 MHz, $CDCl_3$, ppm from TMS): 0.62 (3H, s); 0.99 (3H, s); 2.75 (2H, t); 3.25 (1H, bs); 3.73 (2H, t); 4.69 (1H, dd); 4.80 (1H, dd); 5.85 (1H, dd).

To a solution of 3β-(2-hydroxyethylthio)-5β,14α-card-20(22)-enolide (0.45 g) in 9 ml of dry pyridine, 0.31 ml of mesyl chloride were added dropwise at 0° C. The reaction mixture was stirred for 3 hrs at room temperature and then diluted with ethyl acetate and washed with water. The organic layer was dried over sodium sulfate and evaporated to dryness under reduced pressure to give 0.50 g of the mesylate derivative, which was submitted to the subsequent reaction with 2.5 ml of pyrrolidine in 2.5 ml of absolute ethanol without further purification. The solution was refluxed under nitrogen atmosphere for 3 hrs, then 5 ml of water were added and the resulting mixture extracted with methylene chloride. The organic layer was dried over sodium sulfate and evaporated to dryness under reduced pressure. The crude product was purified by flash-cromatography ($SiO_2$) using methylene chloride/methanol/30% ammonia solution 95/5/1 as eluant; the pure compound so obtained was dissolved in 2 ml of diethyl ether and a solution of 0.080 g of oxalic acid in 1 ml of diethyl ether was added to give 0.31 g of the title compound (I-a) as a white solid, mp 164°–166° C.

$^1$H-NMR (300 MHz, CDCl$_3$, ppm from TMS): 0.62 (3H, s); 0.98 (3H, s); 2.38 (1H, bt); 2.75–2.95 (4H, m); 3.20–3.42 (3H, m); 4.69 (1H, dd); 4.82 (1H, dd); 5.86 (1H, bs).

EXAMPLE 2

3β-(3-Dimethylaminopropylthio)-5β,14α-card-20(22)-enolide Oxalate (I-b)

3β-Mercapto-5β,14α-card-20(22)-enolide (II-a, Prep. 1) (0.13 g) was reacted with 3-dimethylaminopropyl-chloride (0.16 g) in the presence of sodium hydride as described in Ex. 1 to give 0.12 g of the title compound (I-b) as a white solid, mp 136°–138° C.

$^1$H-NMR (300 MHz, CDCl$_3$, ppm from TMS): 0.62 (3H, s); 0.99 (3H, s); 2.20 (1H, dt); 2.38 (1H, bt); 2.58 (2H, t); 2.85 (6H, s); 3.10–3.24 (3H, m); 4.69 (1H, dd); 4.82 (1H, dd); 5.86 (1H, bs).

EXAMPLE 3

3β-(3-(1-Piperazinyl)propylthio)-5β,14α-card-20(22)-enolide Dioxalate (I-c)

3β-Mercapto-5β,14α-card-20(22)-enolide (II-a, Prep. 1) (0.13 g) was reacted with 1-(3-chloropropyl)piperazine dihydrochloride (0.24 g) in the presence of sodium hydride as described in Ex. 1 to give 0.10 g of the title compound (I-c) as a white solid, mp 195°–198° C.

$^1$H-NMR (300 MHz, DMSO-d$_6$, ppm from TMS): 0.55 (3H, s); 0.89 (3H, s); 2.18 (1H, bdt); 3.19 (1H, bs); 4.78 (1H, dd); 4.89 (1H, dd); 5.85 (1H, bs).

EXAMPLE 4

3β-(3-Aminopropylthio)-5β,14α-card-20(22)-enolide Oxalate (I-d)

3β-Mercapto-5β,14α-card-20(22)-enolide (II-a, Prep. 1) (0.15 g) was reacted with 3-chloropropylamine hydrochloride (0.16 g) in the presence of sodium hydride as described in Ex. 1 to give 0.13 g of the title compound (I-d) as a white solid, mp 152°–154° C.

$^1$H-NMR (300 MHz, DMSO-d$_6$, ppm from TMS): 0.55 (3H, s); 0.92 (3H, s); 2.18 (1H, bdt); 2.39 (2H, bt); 2.85 (2H, bt); 3.20 (1H, bt); 4.78 (1H, dd); 4.89 (1H, dd); 5.97 (1H, bs).

EXAMPLE 5

3β-(3-(1-Pirrolidinyl)-2-hydroxypropylthio)-5β,14α-card-20(22)-enolide (I-e)

To a solution of 0.40 g of 3β-mercapto-5β,14α-card-20(22)-enolide (II-a, Prep. 1) and 0.25 g of epichlorohydrin in 8 ml of dimethylformamide under nitrogen atmosphere, 0.055 g of sodium hydride (60% dispersion in mineral oil) were added at −15° C. The reaction mixture was stirred for one hr, then 5.24 ml of 0.5N hydrochloric acid were added and the temperature was left to raise to 25° C. The mixture was extracted with methylene chloride, the organic layer washed with water, dried over sodium sulfate, filtered and evaporated to dryness under reduced pressure. The crude product was purified by flash-chromatography ($SiO_2$) using n-hexane/ethyl acetate 60/40 as eluant to give 0.30 g of 3β-(2,3-epoxy)propylthio- 5β,14α-card-20(22)-enolide as a white pasty solid.

$^1$H-NMR (300 MHz, CDCl$_3$, ppm from TMS): 0.62 (3H, s); 0.99 (3H, s); 2.05–2.25 (3H, m); 2.28 (1H, dt); 2.53–2.85 (5H, m); 3.45 (1H, bs); 4.69 (1H, dd); 4.80 (1H, dd); 5.85 (1H, bs).

A solution of 0.30 g of 3β-(2,3-epoxy)propylthio-5β,14α-card- 20(22)-enolide in 2.5 ml of pyrrolidine was stirred for 48 hrs at room temperature, then the excess base was evaporated and the crude product was dissolved in 1 ml of ethyl acetate. To this solution, 0.063 g of oxalic acid in 2 ml of diethyl ether were added. The precipitate was filtered and washed with diethyl ether, giving 0.26 g of the title compound (I-e) as an amorphous white solid.

$^1$H-NMR (300 MHz, CD$_3$OD, ppm from TMS): 0.64 (3H, s); 0.98 (3H, s); 2.40–2.60 (2H, m); 3.10–3.30 (6H, m); 3.50 (1H, bs); 3.70–3.78 (1H, m); 4.70 (1H, dd); 4.78 (1H, dd); 5.86 (1H, bs).

EXAMPLE 6

3β-(3-Aminopropylthio)-14α-card-4,20(22)-dienolide Oxalate (I-f)

3β-Mercapto-14α-card-4,20(22)-dienolide (II-b, Prep. 2) (0.15 g) was reacted with 3-chloropropylamine hydrochloride (0.15 g) in the presence of sodium hydride as described in Ex. 1 to give 0.11 g of the title compound (I-f)as a white amorphous solid.

$^1$H-NMR (300 MHz, DMSO-d$_6$, ppm from TMS): 0.56 (3H, s); 1.05 (3H, s); 2.18 (1H, bdt); 2.37 (2H, bt); 2.85 (2H, bt); 3.40 (1H, bt); 4.75 (1H, dd); 4.86 (1H, dd); 5.35 (1H, s); 5.97 (1H, bs).

EXAMPLE 7

3β-(3-Aminopropylthio)-14α-card-5,20(22)-dienolide Oxalate (I-g)

3β-Mercapto-14α-card-5,20(22)-dienolide (II-c, Prep. 3) (0.17 g) was reacted with 3-chloropropylamine hydrochloride (0.17 g) in the presence of sodium hydride as described in Ex. 1 to give 0.11 g of the title compound (I-g) as a pale yellow amorphous solid.

$^1$H-NMR (300 MHz, DMSO-d$_6$, ppm from TMS): 0.55 (3H, s); 1.07 (3H, s); 2.19 (1H, bdt); 2.40 (2H, bt); 2.86 (2H, bt); 3.00 (1H, bt); 4.78 (1H, dd); 4.89 (1H, dd); 5.46 (1H, s); 5.97 (1H, bs).

EXAMPLE 8

3β-(3-Aminopropylthio)-5α,14α-card-20(22)-enolide Oxalate (I-h)

3β-Mercapto-5α,14α-card-20(22)-enolide (II-d, Prep. 4) (0.16 g) was reacted with 3-chloropropylamine hydrochloride (0.16 g) in the presence of sodium hydride as described in Ex. 1 to give 0.12 g of the title compound (I-h) as a white amorphous solid.

$^1$H-NMR (300 MHz, DMSO-d$_6$, ppm from TMS): 0.54 (3H, s); 0.85 (3H, s); 2.18 (1H, bdt); 2.39 (2H, bt); 2.85 (2H, bt); 3.00 (1H, bt); 4.77 (1H, dd); 4.87 (1H, dd); 5.96 (1H, bs).

PREPARATION OF INTERMEDIATES

PREPARATION 1

3β-Mercapto-5β,14α-card-20(22)-enolide (II-a)

Into a solution of 5.3 g of 3β-acetylthio-5β,14α-card-20(22)-enolide (IV-a) in 65 ml of methanol/tetrahydrofuran 3/1, gaseous ammonia was bubbled in for 30' and then kept on standing for 3 hrs at room temperature. The mixture was evaporated to dryness under reduced pressure and purified by flash-chromatography (SiO$_2$) using n-hexane/ethyl acetate 77/23 as eluant to give 3.7 g of the title compound (II-a) as a white solid, mp 176°–177° C.

$^1$H-NMR (300 MHz, CDCl$_3$, ppm from TMS): 0.62 (3H, s); 0.99 (3H, s); 2.28 (1H, dt); 2.37 (1H, t); 3.59 (1H, bs); 4.69 (1H, dd); 4.82 (1H, dd); 5.86 (1H, bs).

PREPARATION 2

3β-Mercapto-14α-card-4,20(22)-dienolide (II-b)

2.3 Grams of 3β-acetylthio-14α-card-4,20(22)-dienolide (IV-b) were reacted with gaseous ammonia as described in the Prep. 1 to give 1.0 g of of the title compound (II-b) as a white solid.

$^1$H-NMR (300 MHz, CDCl$_3$, ppm from TMS): 0.62 (3H, s); 1.10 (3H, s); 2.28 (1H, dt); 2.37 (1H, t); 3.38 (1H, bs); 4.69 (1H, dd); 4.81 (1H, dd); 5.31 (1H, s); 5.85 (1H, bs).

PREPARATION 3

3β-Mercapto-14α-card-5,20(22)-dienolide (II-c)

1.4 Grams of 3β-acetylthio-14α-card-5,20(22)-dienolide (IV-c) were treated with gaseous ammonia as described in the Prep. 1 to give 1.1 g of of the title compound (II-c) as a white solid.

$^1$H-NMR (300 MHz, CDCl$_3$, ppm from TMS): 0.62 (3H, s); 1.08 (3H, s); 2.28 (1H, dt); 2.37 (1H, t); 3.40 (1H, bs); 4.69 (1H, dd); 4.83 (1H, dd); 5.43 (1H, s); 5.87 (1H, bs).

PREPARATION 4

3β-Mercapto-5α,14α-card-20(22)-enolide (II-d)

1.3 Grams of 3β-acetylthio-5α,14α-card-20(22)-enolide (IV-d) were treated with gaseous ammonia as described in the Prep. 1 to give 0.90 g of the title compound (II-d) as a white solid.

$^1$H-NMR (300 MHz, CDCl$_3$, ppm from TMS): 0.61 (3H, s); 0.90 (3H, s); 2.30 (1H, dt); 2.36 (1H, t); 3.30 (1H, bs); 4.72 (1H, dd); 4.80 (1H, dd); 5.84 (1H, bs).

PREPARATION 5

3β-Acetylthio-5β,14α-card-20(22)-enolide (IV-a)

Diisopropyl azodicarboxylate (7.7 ml) was added to a solution of 10.3 g of triphenylphosphine in 160 ml of tetrahydrofuran and the mixture was stirred for 30'. A white precipitate formed. To this mixture a solution of 5.6 g of 3α-hydroxy-5β,14α-card-20(22)-enolide and 2.8 ml of thiolacetic acid in 160 ml of tetrahydrofuran was added dropwise and the resulting mixture was stirred for 2 hrs at room temperature. The solvent was evaporated to dryness under reduced pressure and the crude product was purified by flash-chromatography (SiO$_2$) using n-hexane/ethyl acetate 87/13 as eluant to give 5.5 g of the title compound (IV-a) as a white solid, mp 158°–161° C.

$^1$H-NMR (300 MHz, CDCl$_3$, ppm from TMS): 0.61 (3H, s); 0.98 (3H, s); 2.30 (3H, s); 2.38 (1H, t); 4.05 (1H, bs); 4.69 (1H, dd); 4.82 (1H, dd); 5.85 (1H, bs).

PREPARATION 6

3β-Acetylthio-14α-card-4,20(22)-dienolide (IV-b)

2.0 Grams of 3α-hydroxy-14α-card-4,20(22)-dienolide was reacted with diisopropyl azodicarboxylate (2.7 ml), 3.6 g of triphenylphosphine and 1.0 ml of thiolacetic acid in tetrahydrofuran as described in the preparation of IV-a to give 1.8 g of the title compound (IV-b) as a white solid.

$^1$H-NMR (300 MHz, CDCl$_3$, ppm from TMS): 0.60 (3H, s); 1.05 (3H, s); 2.30 (3H, s); 2.36 (1H, t); 4.15 (1H, bs); 4.67 (1H, dd); 4.82 (1H, dd); 5.30 (1H, s); 5.85 (1H, bs).

PREPARATION 7

3β-Acetylthio-14α-card-5,20(22)-dienolide (IV-c)

1.8 Grams of 3α-hydroxy-14α-card-5,20(22)-dienolide was reacted with diisopropyl azodicarboxylate (2.5 ml), 3.3 g of triphenylphosphine and 0.88 ml of thiolacetic acid in tetrahydrofuran as described in the preparation of IV-a to give 1.7 g of the title compound (IV-c) as a white solid.

$^1$H-NMR (300 MHz, CDCl$_3$, ppm from TMS): 0.63 (3H, s); 1.10 (3H, s); 2.32 (3H, s); 2.35 (1H, t); 3.85 (1H, bs); 4.72 (1H, dd); 4.82 (1H, dd); 5.40 (1H, s); 5.85 (1H, bs).

PREPARATION 8

3β-Acetylthio-5α14α-card-20(22)-enolide (IV-d)

2.2 g of 3α-hydroxy-5α,14α-card-5,20(22)-dienolide was reacted with diisopropyl azodicarboxylate (3.0 ml), 4.1 g of triphenylphosphine and 1.1 ml of thiolacetic acid in tetrahydrofuran as described in the preparation of IV-a to give 1.9 g of the title compound (IV-d) as a white solid.

$^1$H-NMR (300 MHz, CDCl$_3$, ppm from TMS): 0.61 (3H, s); 0.97 (3H, s); 2.31 (3H, s); 2.35 (1H, t); 3.70 (1H, bs); 4.69 (1H, dd); 4.82 (1H, dd); 5.86 (1H, bs).

PREPARATION 9

3α-Hydroxy-14α-card-4,20(22)-dienolide (V-a)

To a solution of 5.0 g 3-oxo-14α-card-4,20(22)-dienolide (Fritsch W. et al., *Liebigs Ann. Chem.* 1966, 699, 195) in 250 ml of anhydrous tetrahydrofuran kept at 0° C and under nitrogen 14.5 ml of a 1M solution of Li-selectride© in tetrahydrofuran were added. The mixture was kept at this temperature for 8 hrs and then poured into 500 ml of 10% acetic acid and extracted with ethyl acetate. The organic layer was washed with a saturated solution of sodium bicarbonate, with water, dried over sodium sulfate, filtered and evaporated to dryness under reduced pressure. The crude product was purified by flash-chromatography (SiO$_2$)using ethyl acetate as eluant to give 3.5 g of the title compound (V-a).

$^1$H-NMR (300 MHz, CDCl$_3$, ppm from TMS): 0.62 (3H, s); 1.10 (3H, s); 2.28 (1H, dt); 2.37 (1H, t); 4.08 (1H, bs); 4.69 (1H, dd); 4.81 (1H, dd); 4.92 (1H, bs); 5.85 (1H, bs).

PREPARATION 10

3α-Hydroxy-14α-card-5,20(22)-dienolide (V-b)

To a solution of 7.5 g 3-oxo-14α-card-5,20(22)-dienolide in 370 ml of anhydrous tetrahydrofuran kept at °C. and under nitrogen 21.8 ml of a 1M solution of Li-selectride© in tetrahydrofuran were added. The mixture was kept at this temperature for 12 hrs and then poured into 750 ml of 10% acetic acid and extracted with ethyl acetate. The organic layer was washed with a saturated solution of sodium bicarbonate, water, dried over sodium sulfate, filtered and evaporated to dryness. The crude product was purified by flash-chromatography (SiO$_2$) using ethyl acetate as eluant to give 5.5 g of the title compound (V-b).

$^1$H-NMR (300 MHz, CDCl$_3$, ppm from TMS): 0.60 (3H, s); 1.05 (3H, s); 4.16 (1H, m); 4.76 (2H, m); 5.42 (1H, m); 5.87 (1H, bs).

PREPARATION 11

3α-Hydroxy-5α,14α-card-20(22)-enolide (V-c)

To a solution of 6.0 g 3-oxo-5α,14α-card-20(22)-enolide in 250 ml of anhydrous tetrahydrofuran kept at °C. and under nitrogen 17.3 ml of a 1M solution of Li-selectride© in tetrahydrofuran were added. The mixture was kept at this temperature for 8 hrs and then poured into 600 ml of 10% acetic acid and extracted with ethyl acetate. The organic layer was washed with a saturated solution of sodium bicarbonate, with water, dried over sodium sulfate, filtered and evaporated to dryness under reduced pressure. The crude product was purified by flash-chromatography (SiO$_2$) using ethyl acetate as eluant to give 4.80 g of the title compound (V-c).

$^1$H-NMR (300 MHz, CDCl$_3$, ppm from TMS): 0.61 (3H, s); 0.97 (3H, s); 2.35 (1H, t); 4.28 (1H, m); 4.69 (1H, dd); 4.82 (1H, dd); 5.86 (1H, bs).

PREPARATION 12

3-Oxo -14α-card-5,20(22)-dienolide (VI-a)

To a solution of 10 g of 3α-hydroxy-14α-card-5,20(22)-dienolide (Fritsch W. et al., *Liebigs Ann. Chem.* 1966, 699, 195) in 300 ml of methylene chloride 4.7 g of morpholine-N-oxyde, 0.40 g of tetrapropylammonium perruthenate and 5.0 g of powdered 4 Å molecular sieves were added at room temperature. After 10 hrs the mixture was evaporated to dryness under reduced pressureand the crude product was purified by flash-chromatography (SiO$_2$) using ethyl acetate as eluant to give 8.6 g of the title compound (VI-a).

$^1$H-NMR (300 MHz, CDCl$_3$, ppm from TMS): 0.60 (3H, s); 0.93 (3H, s); 4.76 (2H, m); 5.42 (1H, m); 5.87 (1H, bs).

PREPARATION 13

3-Oxo-5α,14α-card-20(22)-enolide (VI-b)

To a solution of 10 g of 3β-hydroxy-5α,14α-card-20(22)-enolide (Kreiser W. and Nazir M., *Liebigs Ann. Chem.* 1972, 755, 12) in 300 ml of methylene chloride 4.7 g of morpholine-N-oxyde, 0.40 g of tetrapropylammonium perruthenate and 5.0 g of powdered 4 Å molecular sieves were added at room temperature. After 10 hrs the mixture was evaporated to dryness under reduced pressureand the crude product was purified by flash-chromatography (SiO$_2$) using ethyl acetate as eluant to give 8.5 g of the title compound (VI-b).

$^1$H-NMR (300 MHz, CDCl$_3$, ppm from TMS): 0.61 (3H, s); 1.03 (3H, s); 4.69 (1H, dd); 4.82(1H, dd); 4.92 (1H, bs); 5.86 (1H, bs).

We claim:

1. 14-deoxy-14α-cardenolides 3β-thioderivatives, having formula (I):

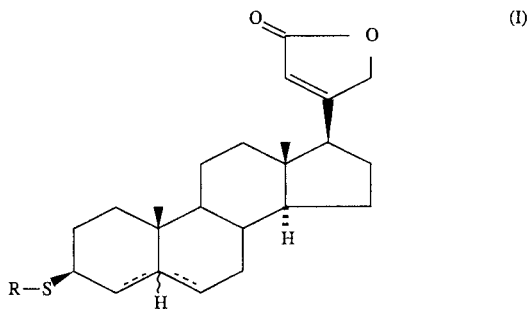

wherein:

the symbol --- represents a single or a double bond;

R is C2–C6 alkyl or C3–C6 alkenyl, substituted by a 2-(2-imidazolinyl) group or one or more OR1 or NR2R3 or C(NH)NR4R5;

wherein:

R1 is C2–C4 alkyl substituted by NR6R7;

R2, R3 are independently C2–C6 alkyl substituted by NR6R7 or R2 and R3 taken together with the nitrogen atom form an unsubstituted or substituted saturated or unsaturated heteromonocylic ring optionally containing another heteroatom chosen from oxygen or sulfur or nitrogen;

R4, R5 taken together with the nitrogen atom form a penta- or hexa-monoheterocyclic ring;

R6, R7 taken together with the nitrogen atom form a saturated or unsaturated penta- or hexa-monoheterocyclic ring optionally containing another heteroatom chosen from oxygen or sulfur or nitrogen, or the pharmaceutically acceptable salts thereof.

2. A compound according to claim 1, which is selected from:

3β-(2-(N-Methyl-N-pyrrolidinium)ethylthio)-5β,14α-card-20(22)-enolide chloride

3β-(2-(1-Pyrrolidinyl)ethylthio)-14α-card-4,20(22)-dienolide

3β-(3-(1-Pyrrolidinyl)propylthio)-14α-card-4,20(22)-dienolide

3β-(2-(1-Pyrrolidinyl)ethylthio)-14α-card-5,20(22)-dienolide

3β-(3-(1-Pyrrolidinyl)propylthio)-14α-card-5,20(22)-dienolide

3β-(2-(1-Pyrrolidinyl)ethylthio)-5α,14α-card-20(22)-enolide

3β-(3-(1-Pyrrolidinyl)propylthio)-5α,14α-card-20(22)-enolide
3β-(2-(1-Pyrrolidinyl)ethylthio)-5β,14α-card-20(22)-enolide
3β-(3-(1-Pyrrolidinyl)propylthio)-5α,14α-card-20(22)-enolide
3β-(2-Morpholinoethylthio)-5β,14α-card-20(22)-enolide
3β-(2-(1-Piperazinyl)ethylthio)-5β,14α-card-20(22)-enolide
3β-(3-(1-Piperazinyl)propylthio)-5β,14α-card-20(22)-enolide
3β-(2-(1-Imidazolyl)ethylthio)-5β,14α-card-20(22)-enolide
3β-(3-(1-Pyrrolidinyl)-2-hydroxypropylthio)-5β,14α-card-20(22)-enolide
3β-(3-(1-Piperazinyl)-2-hydroxypropylthio)-5β,14α-card-20(22)-enolide
3β-(3-(1-Imidazolyl)-2-hydroxypropylthio)-5β,14α-card-20(22)-enolide.

3. A pharmaceutical composition comprising a compound of formula (I) or a pharmaceutically acceptable salt thereof and a pharmaceutically acceptable carrier and/or diluent thereof.

4. An orally or parenterally administrable pharmaceutical composition for the treatment of cardiovascular disorders comprising an effective amount of a compound of formula (I) or an equivalent amount of a pharmaceutically acceptable salt thereof and an excipient therefor.

5. The composition of claim 4 for the treatment of hypertension.

6. The composition of claim 4 for the treatment of cardiac failure.

7. A compound according to claim 1, wherein R is a substituted C2–C6 alkyl.

8. A compound according to claim 1, wherein R is a substituted C3–C6 alkenyl.

9. A compound according to claim 1, wherein R contains a 2-(2-imidazolinyl) group.

10. A compound according to claim 1, wherein R contains the group NR2R3 and wherein R2 and R3 taken together with the nitrogen atom form an unsubstituted or substituted saturated or unsaturated heteromonocyclic ring.

11. A compound according to claim 10, wherein R2 and R3 taken together with the nitrogen atom form an unsubstituted or substituted saturated or unsaturated heteromonocyclic ring further comprising oxygen.

12. A compound according to claim 10, wherein R2 and R3 taken together with the nitrogen atom form an unsubstituted or substituted saturated or unsaturated heteromonocyclic ring further comprising sulfur.

13. A compound according to claim 10, wherein R2 and R3 taken together with the nitrogen atom form an unsubstituted saturated or unsaturated heteromonocyclic ring.

14. A compound according to claim 10, wherein R2 and R3 taken together with the nitrogen atom form a substituted saturated or unsaturated heteromonocyclic ring.

15. A compound according to claim 10, wherein R2 and R3 taken together with the nitrogen atom form an unsubstituted or substituted saturated heteromonocyclic ring.

16. A compound according to claim 10, wherein R2 and R3 taken together with the nitrogen atom form an unsubstituted or substituted unsaturated heteromonocyclic ring.

17. A compound according to claim 1, wherein R contains the group C(NH)NR4R5 and wherein R4 and R5 taken together with the nitrogen atom form a penta- or hexa-monoheterocyclic ring.

18. A compound according to claim 19, wherein R4 and R5 taken together with the nitrogen atom form a penta-monoheterocyclic ring.

19. A compound according to claim 17, wherein R4 and R5 taken together with the nitrogen atom form a hexa-monoheterocyclic ring.

* * * * *

UNITED STATES PATENT AND TRADEMARK OFFICE
CERTIFICATE OF CORRECTION

PATENT NO. : 5,489,582
DATED : February 6, 1996
INVENTOR(S) : Mauro GOBBINI et al.

It is certified that error appears in the above-indentified patent and that said Letters Patent is hereby corrected as shown below:

On the title page, Item [73], the Assignee is written incorrectly. It should read:

--[73] Assignee:  Sigma-Tau Industrie Farmaceutiche Riunite S.p.A, Rome, Italy--

Signed and Sealed this

Fourteenth Day of May, 1996

Attest:

BRUCE LEHMAN

Attesting Officer     Commissioner of Patents and Trademarks